United States Patent [19]
Beck

[11] Patent Number: 5,128,127
[45] Date of Patent: Jul. 7, 1992

[54] INCREASED PROTEIN PRODUCTION IN ANIMALS

[75] Inventor: Lee R. Beck, Lebanon, Ohio

[73] Assignee: Stolle Research & Development Corp., Cincinnati, Ohio

[21] Appl. No.: 307,806

[22] Filed: Feb. 8, 1989

[51] Int. Cl.$^5$ .................. A61K 39/00; A23B 4/00
[52] U.S. Cl. ........................... 424/88; 424/89; 424/92; 426/2; 426/641; 426/644; 426/657
[58] Field of Search ............... 424/88, 89, 92; 426/2, 426/641, 644, 657

[56] References Cited

U.S. PATENT DOCUMENTS

| | | | |
|---|---|---|---|
| 3,128,230 | 4/1964 | Heinbach | 167/78 |
| 4,284,623 | 8/1981 | Beck | 424/85.8 |
| 4,324,782 | 4/1982 | Beck | 424/87 |
| 4,636,384 | 1/1987 | Stolle et al. | 424/87 |
| 4,732,757 | 3/1988 | Stolle et al. | 424/87 |

OTHER PUBLICATIONS

Flint et al, *Hannah Res.* pp. 123–127, 1985.
Srinivason et al, *Indian Veter. Journal,* vol. 54, pp. 1–5, 1977.
Mersmann, H. J., *Prog. Food Nutri. Sci.* 11:175–201 (1987).
Williamson, E. D. et al., *Livestock Prod. Sci.* 12:251–264 (1985).
Speer, V. C., *Designing Foods,* pp. 273–277, 1988, National Academy Press, Washington, DC.
National Research FCouncil, *Designing Foods,* Chapter 6, pp. 115–132, 1988, National Academy Press, Washington, DC.
Schelling, G. T. et al., *Designing Foods,* pp. 200–207, 1988, National Academy Press, Washington, DC.
Spencer, G. S. G. et al., *Livestock Prod. Sci.* 10:25–37 (1983).
Spencer, G. S. G. et al., *Anim. Prod.* 40:523 (1985).
Sun, M., *Science* 240:136 (1988).

Primary Examiner—Johnnie R. Brown
Assistant Examiner—Abdel A. Mohamed
Attorney, Agent, or Firm—Sterne, Kessler, Goldstein & Fox

[57] ABSTRACT

The present invention provides a method of increasing the ratio of body protein to fat in a animal by maintaining the animal in a hyperimmune state. The invention also provides a method of increasing carcass protein levels in animals. The invention further provides a method for producing lean, low-fat meat for human or animal consumption.

12 Claims, 2 Drawing Sheets

INCREASED PROTEIN PRODUCTION IN ANIMALS

BACKGROUND OF THE INVENTION

1. Field of the Invention

The present invention relates to a method for the production of lean meat-containing animals. Specifically, the invention relates to a method for the regulation of protein and fat content in animals by hyperimmunization.

2. Brief Description of the Background Art

The production of food animals containing a relatively high protein content and a relatively low fat content is a major goal of food providers. See Sun, M., *Science* 240: 136 (1988); and "Designing Foods: Animal Product Options in the Marketplace," Committee on Technological Options to Improve the Nutritional Attributes of Animal Products, Board on Agriculture, National Research Council, National Academy Press, Washington, D.C., 1988.

Animal food products are a major source of fat calories in the consumer diet, supplying about 36% of the caloric intake. Animal food products account for 57% of the fat consumed in the typical American diet and have been implicated as an important factor contributing to the development of heart disease and other related ailments. The American Cancer Society (1984), American Heart Association (1986), National Institutes of Health (1984) and the National Research Council (1982) have all recommended that 30% or less of the total caloric intake of adults be in the form of fat. *Designing Foods supra*, p. 15. Although consumer eating habits are changing and less red meat is being consumed, a recent report from the National Academy of Sciences, which evaluated ways to reduce the contribution of animal food products to the dietary fat intake, concluded that "the real solution lies in the production of leaner animals" Designing Foods, supra, p 3.

Current methods of producing lean animals and meat utilize hormones to increase the body protein to fat ratio, "Designing Foods", supra, and Mersmann, H. J., *Prog. Food Nutr. Sci.* 11:175-201 (1987). Hormones that have been used to regulate the carcass ratio of protein to fat include anabolic steroids, growth hormone, and adrenergic agonists.

Anabolic steroids have been effectively administered to ruminant species and especially to beef cattle for the purpose of manipulating carcass protein content. A ruminant animal being fed anabolic steroids produces more muscle and less fat. However, anabolic steroid treatments are not effective in non-ruminant species. In addition, consumer concern over possible residual levels of anabolic steroids in the food product itself have led to pending legislation in many countries proposing a complete ban of this method. The European Community banned the use of steroids in 1988.

Changes in body composition induced by growth hormone are similar to those induced by anabolic steroids; that is, growth hormone induces the accumulation of more muscle and less fat. In addition, growth hormone is effective in both ruminant and nonruminant species. Research efforts in this area have recently been focused on the creation of genetically modified animals containing a regulatable growth hormone gene such as zinc-regulatable human growth hormone. Sun, M., *Science* 240:136 (1988), and Miller, C., *Gen. Eng. News*, May 1987, p. 7. In theory, the zinc-regulatable human growth hormone gene would be induced or repressed at appropriate periods in the animal's growth by altering the levels of zinc in the diet. However, this approach has not been completely successful. In pigs the gene appears to be "leaky," that is, continuously expressing whether or not the diet is supplemented with zinc, Marx, J. L. *Science* 242:32-33 (1988). Because of the overproduction of growth hormone, the transgenic growth hormone pigs have some serious abnormalities; females are sterile, and both males and females are generally susceptible to arthritis and gastric ulcers which often are fatal. Marx, J. L., *Science* 242:32-33 (1988). In addition, as with steroid treatment, consumer acceptance of meat from growth hormone genetically engineered cattle has been a major problem. Sun, M., *Science* 240:136 (1988).

Analogs of the $\beta$-adrenergic agonists epinephrine and norepinephrine, especially clenbuterol and cimaterol, have been used to increase carcass protein levels in food animals. Muir, L. A., *Designing Foods, supra*, pp. 184-193. These agonists, while they have only small effects on weight gain and feed efficiency in the animals, tend to stimulate lipolysis and thus change the total body composition to a higher protein, less fat composition. However, chronic feeding may cause hypertrophy of skeletal muscle and some food species, such as chicken, are poor responders. Also, $\beta$-agonists are usually included in the diet and therefore are not suitable for use with grazing animals. Lastly, as with the other hormone treatments, there is a strong public opposition directed against eating meat from $\beta$-agonist-treated animals.

Normally, upon exposure to a foreign antigen, e.g., a bacterium, the immune system of the host will produce antibodies that will neutralize the effects of the antigen. Exposure to such foreign antigens can occur either naturally, or deliberately by administration of the antigen in vaccine form. The latter is generally referred to as active immunization of the host species exposed to the antigen. The antibodies produced in response to such vaccination are homologous to said given species of animal, and are epitopic to the antigen. In general, merely inducing an immune state in an animal does not alter the levels of carcass fat or protein, Williamson, E. D., et al., *Livestock Prod. Sc.* 12:251-264 (1985).

To avoid the problems associated with exogenous hormone administration, attempts have been made to regulate animal growth immunologically, by actively immunizing the animal against a specific component or hormone, the lack of which promotes the development of a relatively lean animal. For example, a single injection, into growing rats, of antibodies raised against fat cell plasma membranes, significantly lowered the levels of body fat and the number of fat cells in the rats for a period of several months. Flint, D. J., et al. *Hannah Res.* (1985), pp. 123-127. However, immunizing against fat cells per se makes it difficult to control the level of body fat on an animal. Animals that are overly lean would suffer from some of the same serious problems that the transgenic growth hormone-containing pigs do due to their overly lean growth, for example, sterility. In addition, meat from overly lean animals has a tendency to be tough, and lacks succulence and flavor. Speer, V. C., in *Designing Foods supra*, pp. 273-277. A minimum of 3% fat (uncooked) has been recommended as the minimum percentage required for palatability of broiling cuts of meat. Savell, J. W. et al., *Designing Foods, supra*, pp.345–355.

Attempts have also been made to increase growth hormone levels in growing animals by immunizing lambs and beef cattle against somatostatin, the hormone responsible for suppression of growth hormone. This method has also been tried on sheep and has been recently reviewed. *Designing Foods, supra*, Chapter 6, pp. 115–132; and Schelling, G. T. et al., *Designing Foods, supra*, pp. 200–207. In theory, by immunizing against somatostatin, the levels of somatostatin would decrease and thus the levels of growth hormone increase. However, this method has produced conflicting results. Spencer, G. S. G., et al., *Livestock Prod. Sc.* 10: 25–37 (1983). Lambs immunized repeatedly against somatostatin grew larger, faster, and were heavier than non-immunized lambs but there was no change in the proportion of muscle or fat. One study, which compared the carcass composition of lambs repeatedly immunized against somatostatin using lambs of equal weight (rather than equal age), suggested that at any given weight, the carcass of the immunized lamb was leaner. Spencer, G. et al., *Anim. Prod* 40:523 (1985). However, repeatedly immunizing with a purified hormone such as somatostatin is relatively expensive when treating large numbers of herd animals.

It has been known in the prior art to produce a hyperimmune state in an animal wherein that hyperimmune state produced a milk having a variety of therapeutic effects. Beck, for example, has disclosed a milk containing antibody to *Staphylococcus mutans* that has dental caries-inhibiting effects (Beck, U.S. Pat. No. 4,324,784; British Patent 1,505,513). Beck has also described a milk having anti-arthritic properties, U.S. Pat. No. 4,732,757, and has patented a method of treating inflammation using milk from hyperimmunized cows, Beck, U.S. Pat. No. 4,284,623. Stolle et al. have disclosed a method of using milk from a hyperimmunized cow for the treatment of diseases of the vascular and pulmonary systems, U.S. Pat. No. 4,636,384.

In addition, in U.S. Pat. No. 4,636,384, there was disclosed a method of lowering blood lipid levels and treating lipid-associated vascular disorders, as well as treating macrophage-related pulmonary disorders, comprising feeding test animals and humans milk derived from cows maintained in a hyperimmune state.

Other authors have noted the ability to derive therapeutic products from the milk of mammals by specifically immunizing or hyperimmunizing those animals against a known antigen. Heinbach, U.S. Pat. No. 3,128,230, Singh (U.S. Pat. No. 3,911,108), Peterson (U.S. Pat. No. 3,376,198 and Canadian Patent 587,849), Holm (U.S. application (published) Ser. No. 628,987), and Tannah et al. (British Patent 1,211,876), and Biokema S. A. (British Patent 1,442,283).

However, no suggestion or speculation is made in any of these references that the hyperimmune state itself alters the metabolism of the animal so as to increase the ratio of body carcass protein to fat. Placing an animal in a hyperimmune state has been reported to increase the concentration of proteins in the serum, Srinivasan, V. A., et al., *Indian Veterinary Journal* 54:1–5 (1977); and Janos, S. et al., *Magy Allatory Lap* 20:487–490 (1965). However, changes in serum protein levels do not necessarily correlate with levels of carcass protein and fat content, and neither report noted any effect of hyperimmunization on the carcass protein or fat content of the animal.

Thus there remains a need for methodology for the production of lean food animals. Such would be methodology that does not physiologically impair the animal. Such methodology would result in a food product acceptable to the consumer, yet be technically simple, and economically applicable to large numbers of herd animals and especially to grazing animals.

SUMMARY OF THE INVENTION

The present invention provides a method of increasing the ratio of body protein to fat in animals by maintaining the animal in a hyperimmune state.

The invention also provides a method of increasing carcass protein levels in animals.

The present invention further provides a method for producing lean, low-fat meat for human or animal consumption.

DESCRIPTION OF THE PREFERRED EMBODIMENTS

Figure 1A:
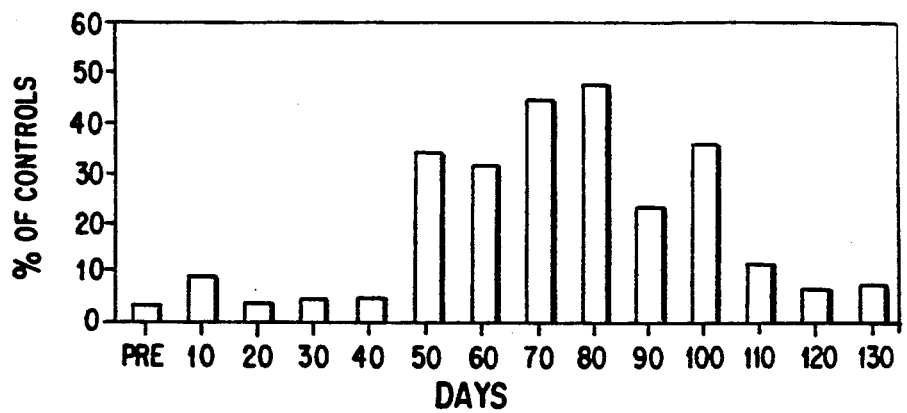
FIG. 1(A–C) compares the serum antibody response of three cows hyperimmunized with simian rotavirus.

The present invention relates to the production of lean meat and animals.

By the term "lean meat" is meant meat with a fat content of 7.3% or less (uncooked). This figure was derived by Savell et al. and represents the maximum amount of fat that should be present in cuts of meat to ensure nutritional merit. The calculation of this figure takes into consideration an assumption of a) a 2000 kcal/day food intake per person, b) no more than 30% (600 kcal) of those 2000 cal/day from fat, c) of the calories from fat, no more than 25% (150 kcal) from fat in red meat such as beef, pork, mutton and lamb, d) no more than 16.6 g fat/day from red meat, and e) two, four ounce servings or 226.8 g total (uncooked weight) of meat per day. Savell, J. W. et al., *Designing Foods, supra*. pp. 345–355.

By the term "administered" is intended any method of treating an animal with a substance such as orally, intranasally, parenterally (intravenously, intramuscularly, or subcutaneously), or rectally, in a pharmaceutically accepted vehicle.

By the term "food animal" is intended any animal that is consumed as a source of protein in the diet of humans or other animals. Typical food animals include bovine animals, for example cattle; ovine animals, for example sheep; swine, for example pigs; fowl, for example chickens and turkeys; rabbit and the like.

The invention is based on the surprising discovery that the carcass and especially the meat of animals which are in a hyperimmune state contain more protein and less fat than animals not in a hyperimmune state and that when a growing food animal is induced to a hyperimmune state, the development of the animal is such that it is relatively leaner than animals not in a hyperimmune state. The induction of immune sensitivity alone is insufficient to enhance this lean growth characteristic.

Many features may influence the deposition of fat in the carcass such as breed, nutrition, sex and live weight. Generally, the heavier the carcass weight, the greater the amount of fat laid down. Therefore, if the rate of fat deposition is slowed, a leaner animal is produced when compared to an untreated animal of the same weight.

To induce the hyperimmune state, the preferred dose range of the antigen is equal to or greater than 50% of the dosage necessary to cause primary immune sensitization of the animal. Thus, there is a booster dosage threshold below which the maximum hyperimmune properties are not produced in the growing animal, even though the animal may be in what is normally called an immune state. The process of producing a hyperimmune animal has been disclosed in Beck, U.S. Pat. No. 4,284,623, which is herein incorporated by reference to the extent that it provides details of the production of the hyperimmune state. In summary, the process comprises the following steps: a) antigen selection, b) sensitization of the animal by primary immunization, c) testing the serum of the animal to confirm sensitivity induction, and d) administering boosters of appropriate dosage to induce and maintain a hyperimmune state.

Any antigen or combination of antigens may be employed. The antigens can be bacterial, viral, protozoan, fungal, cellular or any other substances to which the immune system of the animal will respond. Examples of bacterial species which may be used as a source of antigenic materials include Corynebacteria, Pneumococci, Aerobacter, *Escherichia coli*, Klebsiella, Hemophilus, Proteus, Shigella, Propinibacter, Salmonella, Streptococci, Staphylococci, Neisseria, enteric bacilli and bacteroides, pseudomonades, Yeisinia, Francisella, Pasteurella, Brucella, aerobic spore-forming bacilli, Clostridia, Mycobacteria, Actinomycetes, Spirochetes, Rickettsie, and Chlamydia.

The critical aspect of antigen selection is only that the antigen(s) must be capable of inducing immune and hyperimmune states in the animal. Preferably, noninfectious polyvalent bacterial agents are used. One preferred vaccine is a mixture of polyvalent bacterial antigens, described in detail in Example 1 below.

The advantage of polyvalent bacterial vaccines is that they are good inducers of the immune and hyperimmune response in animals and that they are economical to administer to large numbers of animals. Because the method of the invention relies only upon induction of the hyperimmune state in the animal, and not upon induction of an immune state against a specific antigen, any cost-effective vaccine capable of inducing the immune and hyperimmune response may be used.

The antigen(s) can be administered by any method that causes sensitization. In one method, a vaccine composed of antigen derived from $1 \times 10^6$ to $1 \times 10^{20}$, preferably $10^8$ to $10^{10}$, most preferably $2 \times 10^8$, heat-killed bacteria is administered by intramuscular injection. However, other methods such as intravenous injection, intraperitoneal injection, subdermal implants, rectal suppositories, oral administration and scratching the skin with the vaccine composition may be used if they are sufficient to induce sensitization.

It is necessary that the animal become sensitive to the antigen, because a hyperimmune state is only induced in an animal which has been immunologically induced to respond to the antigen. An animal which does not immunologically respond to the presence of an antigen is incapable of inducing the hyperimmune state.

There are a number of methods known to those skilled in the art of immunology to test for sensitivity (*Methods in Immunology and Immunochemistry*, Williams, C. A. et al., Academic Press, New York, Volumes 1-5 (1975)). The preferred method when using a polyvalent vaccine comprising multiple bacterial species as the antigen is to test for the presence of agglutinating antibodies in the serum of the animal before and after challenge with the vaccine.

Antibody response or production is characterized by having two phases, a primary phase and a secondary phase. The primary phase can be divided into a lag phase, growth phase and a decline phase. The lag phase is the interval between the injection of the antigen and the appearance of the first antibody in the body. The growth phase is the time during which the antibody levels rise to a peak. Peak antibody levels are obtained at various times depending on the antigen. Typically antibody levels remain at the peak for a few days and then decline. The decline phase is the time during which antibody levels decline from the peak. During the primary phase antibody levels may decline at a rate of about 7 to 10 percent per day.

It is well known and generally accepted by those skilled in the art that the secondary phase requires a second exposure to antigen. The secondary phase, like the primary, is characterized by lag, growth and decline. The lag period, however, is much shorter than the primary lag period, the growth phase is more rapid and the peak levels are higher. The duration of each phase and the peak levels vary from antigen to antigen and depend, to some degree, on the dose and the vehicle used for administration of the vaccine antigen.

The term hyperimmunization implies something significantly different from the typical response pattern that one would expect following a vaccination. In a hyperimmune state, the response of the immune system of an animal is not divided into a primary and secondary phase. Following an initial lag period, antibody levels increase during a growth phase and reach a plateau. The peak levels are maintained with no apparent secondary response for at least several weeks before beginning a slow gradual decline phase. The hyperimmune response results in a greater stimulation of the immune system as a whole and includes an enhanced response to the antigen. One manifestation of this enhanced response is a greater total antibody production than can be achieved using the conventional method of immunization. The state of hyperimmunization is immediately obvious to anyone skilled in the art of immunology simply by comparing the pattern of antibody response.

In one embodiment, induction and maintenance of the hyperimmune state in the sensitized animal is accomplished by repeated booster administration at fixed time intervals using the same vaccine that is used to achieve the primary sensitization. A two-week booster interval is optimal for polyvalent bacterial antigens. However, any time interval in which it is insured that the animal does not pass from a hyperimmune state to a state of immune tolerance to the antigen is acceptable. An animal which passes into a state of immune tolerance to an antigen will cease to make antibodies to the antigen and loses the beneficial effects of the hyperimmune state on the carcass protein and fat levels.

In a preferred embodiment, hyperimmunization of food animals is achieved by a single administration of microencapsulated vaccine. The microencapsulated vaccine results in a constant, pulsed release of the vaccine into the animal and eliminates the need for repetitive injections. In addition, a greater immune response, as measured by antibody production, is achieved using a controlled release vaccine. Many different compositions for the slow release of vaccines have been described which would be applicable to the method of the invention, for example, as described in Sanders, H. J., Chem. & Engineering News, Apr. 1, 1985, pp. 30–48.

Generally, the antigen-containing shaped matrix materials are formed from polymers of biocompatible material, preferably biodegradable or bioerodable materials, preferably polylactic acid, polyglycolic acid, copolymers of lactic and glycolic acids, polycaptolactone, copolyoxalates, proteins such as collagen, fatty acid esters of glycerol, and cellulose esters. These polymers are well known in the art and are described, for example, in U.S. Pat. No. 3,773,919; U.S. Pat. No. 3,887,699; U.S. Pat. No. 4,118,470; U.S. Pat. No. 4,076,798, all incorporated by reference herein.

In one embodiment, antigens are encapsulated in such matrix materials, preferably as microspheres of between 1–500 microns diameter, and most preferably 10–250 microns. The encapsulation processes are conventional and comprise phase separation methods, interfacial reactions, and physical methods. Many combinations of matrices and many concentrations and mixtures of antigens may be employed, in order to provide for optimal rates of release of bacterial antigens to the host body from the microparticles. These combinations can be determined by those skilled in the art without undue experimentation.

In another embodiment, it is possible to induce a hyperimmune state by combining different immunization procedures, e.g., simultaneously administering microencapsulated and liquid antigen, or intramuscular injection for primary immunization, and booster doses by oral administration or parenteral administration by microencapsulation means. Many different combinations of primary immunization and hyperimmunization are known to those skilled in the art, for example, as described in *Antibodies, A Practical Approach*, D. Catty, ed., vol. I and II, IRL Press, Washington, D.C., 1988.

The method of the invention is applicable to any animal used as a source of food and especially as a source of meat such as mutton and lamb from sheep; beef and veal from cattle; pork from pigs; poultry meat including meat from chickens and turkeys, and rabbit meat.

In a highly preferred embodiment animals are hyperimmunized while still growing and maturing into the adult state. The first immunization may be given as soon as the animal is competent to immunologically respond to the antigen. Animals immunologically competent to respond to the antigen are also capable of being placed in a hyperimmune state.

In another embodiment, mature, non-growing animals are hyperimmunized. Hyperimmunization of mature animals provides all the beneficial effects of the hyperimmunized state to the animal, such as a decrease in carcass lipid content.

An advantage of the method of the invention is that hyperimmunized animals do not become 'overly lean' and thus do not suffer from the physiological complications, such as sterility, that accompany the overly lean characteristic. No detrimental effects of maintaining an animal in a hyperimmune state are known. The applicant has maintained cows in a hyperimmune state since 1974 and noticed no apparent harmful effects on the cow's physiology or milk production.

Another advantage of the method of the invention is that it does not involve hormone administration or genetically altered animals, so that consumer concerns about hormone contamination in lean meat from hyperimmunized animals is not a factor.

The method of the invention is also applicable to weight control in domestic animals and pets, such as cats, dogs, horses, rabbits and the like, especially when practiced using a prolonged-release vaccine composition.

Having now described the invention in general terms, the same will be further described by reference to certain specific examples that are provided herein for purposes of explanation only and are not intended to be limiting unless otherwise specified.

EXAMPLE 1

INDUCTION OF A HYPERIMMUNE STATE IN COWS a) Induction of a Hyperimmune State in Cows with a Mixed Bacterial Vaccine A bacterial culture, containing the spectrum of bacteria shown in Table 1 below as obtained from the American Type Culture Collection, was reconstituted with 15 ml of growth medium and incubated overnight at 37° C. Once good growth was obtained, approximately one-half of the bacterial suspension was employed to inoculate one liter of broth, with the inoculate being incubated at 37° C. The remaining suspension was transferred to sterile glycol tubes and stored at $-20°$ C. for up to six months.

After good growth was visible in the culture, the bacterial cells were harvested by centrifugation of the suspension at a g force which separates the cells from the growth medium by pelleting them. The growth medium was decanted and the bacterial pellet resuspended in sterile saline solution. The bacterial sample was centrifuged three times to wash the medium from the cells. After the third sterile saline wash, the bacterial pellet obtained upon centrifugation was resuspended in a small amount of double distilled water.

The medium-free bacterial suspension was heat-killed by placing the suspension in a glass flask in an 80° C. water bath overnight. The viability of the broth culture was tested with a small amount of heat-killed bacteria, as follows: broth was inoculated with heat-killed bacteria, incubated at 37° C. for five days and checked daily for growth. For the safety of the cow, the bacteria should be killed for use in the vaccine. The heat-killed bacteria were lyophilized until dry. The dry bacteria were then mixed with sterile saline solution to a concentration of about $2.2 \times 10^8$ bacterial cells/ml saline (1.0 optical density units at 660 nm).

TABLE 1

| Bacteria List - S100 Vaccine | | | | |
|---|---|---|---|---|
| Name | Growth Media | Gram + or − | ATTC # | % by Weight |
| 1. Staph. aureus | 1 | + | 11631 | 4.28 |
| 2. Staph. epidermidis | 1 | + | 155 | 0.67 |
| 3. Strep. pyogenes, A. Type 1 | 1 | + | 8671 | 6.43 |
| 4. Strep. pyogenes, A. Type 3 | 1 | + | 10389 | 0.67 |
| 5. Strep. pyogenes, A. Type 5 | 1 | + | 12347 | 4.28 |
| 6. Strep. pyogenes, A. Type 8 | 1 | + | 12349 | 0.67 |
| 7. Strep. pyogenes, A. Type 12 | 1 | + | 11434 | 1.34 |
| 8. Strep. pyogenes, A. | 1 | + | 12972 | 2.00 |

TABLE 1-continued
Bacteria List - S100 Vaccine

| Name | Growth Media | Gram + or − | ATTC # | % by Weight |
|---|---|---|---|---|
| Type 14 | | | | |
| 9. *Strep. pyogenes*, A. Type 18 | 1 | + | 12357 | 12.90 |
| 10. *Strep. pyogenes*, A. Type 22 | 1 | + | 10403 | 4.28 |
| 11. *Aerobacter aerogenes* | 1 | − | 884 | 4.28 |
| 12. *Escherichia coli* | 1 | − | 26 | 4.28 |
| 13. *Salmonella enteritidis* | 1 | − | 13076 | 8.56 |
| 14. *Pseudomonas aeruginosa* | 1 | − | 7700 | 8.56 |
| 15. *Klebsiella pneumoniae* | 1 | − | 9590 | 0.67 |
| 16. *Salmonella typhimurium* | 1 | − | 13311 | 2.14 |
| 17. *Hemophilus influenzae* | 1 | − | 9333 | 0.67 |
| 18. *Strep. mitis* | 2 | + | 6249 | 6.43 |
| 19. *Proteus vulgaris* | 1 | − | 13315 | 4.28 |
| 20. *Shigella dysenteriae* | 1 | − | 11835 | 8.56 |
| 21. *Diplococcus pneumoniae* | 1 | + | 6303 | 0.67 |
| 22. *Propionibacter acnes* (anaerobe) | 1 | + | 11827 | 2.00 |
| 23. *Strep. sanguis* | 3 | + | 10556 | 4.28 |
| 24. *Strep. salivarius* | 1 | + | 13419 | 4.28 |
| 25. *Strep. mutans* | 1 | + | 25175 | 0.67 |
| 26. *Strep. agalactiae* | 1 | + | 13813 | 2.14 |

Growth media (1) is BioTek Broth; (2) is Tryptic Soy Broth plus Supplement C; (3) is Thioglycolate Broth. All media was obtained from Difco Labs and prepared according to their specifications.

Each vaccination contains 934 mg of bacteria. Animals such as cattle become hyperimmunized when 5 ml samples of the polyvalent liquid vaccine are injected daily. Antibody (IgG) titer levels for the injected cattle were determined periodically by taking optical density readings at 410 nm of antibody-containing fluid samples obtained from cow's milk.

b) Preparation of a Controlled Release Vaccine.

A heat killed rotaviral antigen (SA11 Rotavirus; ATCC No. VR-899) was propagated in MA104 cells (MA Bioproducts) in Opti-MEM medium plus 5% fetal calf serum (Gibco). The virus was microencapsulated by a conventional phase-separation process to prepare a polyvalent antigen-containing microparticle product. The formed matrix material was a copolymer of lactic and glycolic acid in a ratio of 85% lactide and 15% glycolide. The size range of the microspheres was 20 to 150 μm. The microspheres contained approximately 50% by weight of the mixed bacterial antigen. The vehicle used for this experiment was physiological saline.

Figure 1B:
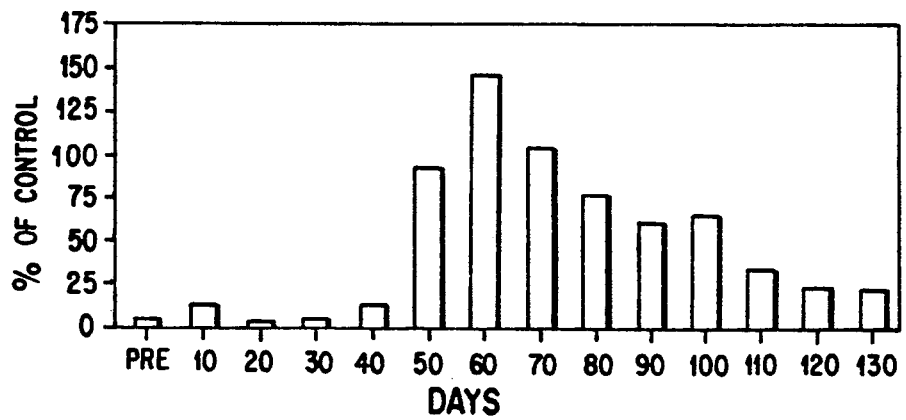
Figure 1C:
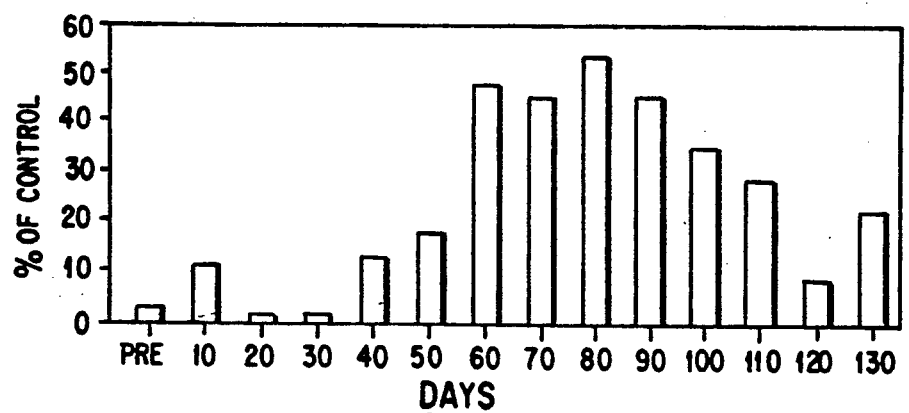
Figure 2:
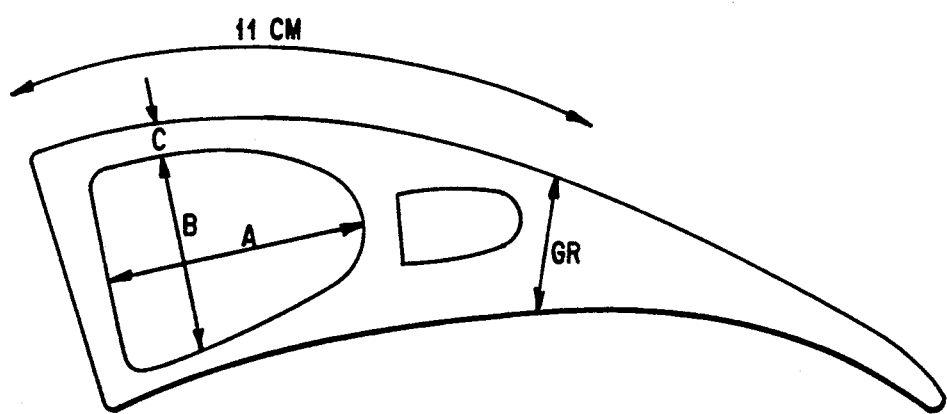
FIG. 2 is a diagram which shows the location where the rib eye muscle was measured for its width (position 'A'), and its depth (position 'B') and where measurements were made of backfat thickness (positions 'C' and 'GR').

FIG. 1(A-C) compares the serum antibody response in three cows hyperimmunized with the heat-killed simian rotavirus vaccine using the controlled release delivery system described above.

As is shown in FIG. 1, each of the three cows maintained high levels of the rotavirus-specific anti-SAII antibody in their serum for at least three months. These data further demonstrate the utility of a viral vaccine in the induction of the hyperimmune state.

c) Preparation of a Vaccine of Unknown Antigen Composition

We have discovered that bee honey contains a diverse group of antigens, the composition of which is unknown. The antigen in honey is capable of inducing a hyperimmune state when injected in cows.

For example, a dose of 1 ml of honey diluted 1:5 in water was injected into 5 cows, once a week for 5 consecutive weeks, then once every 2 weeks for 6 months. Milk collected between the third and sixth months and tested for antibody demonstrated that this vaccination procedure and antigen were able to induce and maintain the hyperimmune state in the cow.

This example is included to illustrate the points that the exact composition of the antigen need not be known to induce the hyperimmune state needed to practice the invention, and that any antigen or combination of antigens either known or unknown might be used.

EXAMPLE 2

EFFECT OF S-100 ANTIGEN ON THE CARCASS COMPOSITION OF THE GROWING LAMB

Twenty-eight weaned Romney lambs weighing 31-32 kg and aged 14 weeks were fed a diet of rye grass and white clover (a standard pasture diet). Eight lambs were slaughtered just prior to starting the experiment (pre-experimental group). The remaining 20 animals were divided into two groups of ten. One group of 10 was subcutaneously injected in the neck region with the S100 antigen described above (treated group); the other group of 10 acted as the control group. The S100 antigen was mixed in 0.9% NaCl and each treated lamb was injected with 2 ml which provided 3.8 to 4 mg of the antigenic material. The treated group received one injection per week for the first three weeks. Additional injections in biweekly intervals. During the 20-week experimental period, the treated lambs received a total of 12 injections. The control group were injected with 0.9% NaCl using the same protocol as the treated animals. At slaughter the liveweight of the lambs was 50 kg (22 kg carcass weight).

The thickness of the rib eye muscle and backfat of the two groups of lambs were examined as indicators of the muscle and fat content of the animals. The backfat thickness was measured at positions C and GR as shown in FIG. 3. Measurements of backfat thickness are a standard method of estimating body fat and were first used to measure the thickness of subcutaneous fat on live animals by Hazel et al., *J. Anim. Sci.* 11: 313 (1952). The GR measurement is a measure of the fat depth in mm over the 12th rib at a point 11 cm from the back bone and is an indicator of the fat content of the carcass. The GR measurement is used to grade the lamb carcasses by the New Zealand meat industry. The eye muscle width and depth are also standard measurements of body protein content and were examined at positions A for the width and B for the depth as defined on FIG. 3.

TABLE 2

Effect of S-100 Vaccine on Eye Muscle and Carcass Backfat Measurements

| | Rib Eye Muscle | | | Carcass Backfat | |
|---|---|---|---|---|---|
| | A (mm) | B (mm) | Area (cm$^2$) | C (mm) | GR (mm) |
| Pre-expt | 51.0 ± 0.47 | 24.5 ± 0.36 | — | 2.06 ± 0.28 | — |
| Control | 51.9 ± 0.48 | 30.1 ± 0.43 | 11.9 ± 0.17 | 8.2 ± 0.80 | 21.40 ± 2.05 |
| Treated | 55.2 ± 0.99 | 30.6 ± 0.66 | 13.3 ± 0.38 | 5.4 ± 0.71 | 17.80 ± 1.08 |

TABLE 2-continued

<table>
<tr><td colspan="6">Effect of S-100 Vaccine on Eye Muscle<br>and Carcass Backfat Measurements</td></tr>
<tr><td></td><td colspan="3">Rib Eye Muscle</td><td colspan="2">Carcass Backfat</td></tr>
<tr><td></td><td>A<br>(mm)</td><td>B<br>(mm)</td><td>Area<br>($cm^2$)</td><td>C<br>(mm)</td><td>GR<br>(mm)</td></tr>
<tr><td>Significance</td><td>*</td><td>NS</td><td>*</td><td>*</td><td>NS</td></tr>
</table>

As is shown in Table 2, in growing lambs maintained in a hyperimmune state there was a 10% increase in the rib eye muscle width at position "A" and muscle area, and a decrease in the backfat content at positions "GR" and "C" which covers this area. There was no change in the depth of the muscle at position "B."

No significant difference in the growth rates or carcass weights were observed between the control and the treated lambs (Table 3).

Taken together, the results shown in Tables 2 and 3 show that animals maintained in a hyperimmune state contain more muscle and less backfat and are relatively leaner when compared to nonhyperimmune animals of equal weight.

EXAMPLE 4

Chemical Composition of the Carcass

The chemical composition of the carcasses of the two groups of lambs described in Experiment 2 was performed. As is shown in Table 4, lambs maintained in a hyperimmune state contained approximately 3.2% of their carcass weight as protein when compared to values obtained for nonhyperimmune animals (only 2.6% of their carcass weight as protein). In addition, hyperimmune animals contained only 6.4% of their carcass weight as lipid while nonimmune animals had a mean lipid value of 7.6% of their carcass weight. The ash content of hyperimmune animals was also slightly higher being 0.94% of the carcass weight as compared to only 0.86% of the carcass weight of the nonhyperimmune animals. Maintaining the lambs in a hyperimmune state decreased the lipid content of the carcass by 12% (p<0.01) and increased the protein content of the carcass by 24% (p<0.001).

TABLE 4

<table>
<tr><td colspan="9">Chemical Composition of Carcass (mean values)</td></tr>
<tr><td></td><td colspan="8">Chemical</td></tr>
<tr><td></td><td colspan="2">Moisture</td><td colspan="2">Fat</td><td colspan="2">Protein</td><td colspan="2">Ash</td></tr>
<tr><td></td><td>(kg)</td><td>%</td><td>(kg)</td><td>%</td><td>(kg)</td><td>%</td><td>(kg)</td><td>%</td></tr>
<tr><td>Pre-expt</td><td>7.17 ± 0.16</td><td>56.0</td><td>2.78 ± 0.21</td><td>21.7</td><td>1.99 ± 0.11</td><td>15.6</td><td>0.61 ± 0.026</td><td>4.8</td></tr>
<tr><td>Control</td><td>10.74 ± 0.23</td><td>46.6</td><td>7.80 ± 0.27</td><td>35.8</td><td>2.63 ± 0.06</td><td>11.9</td><td>0.87 ± 0.11</td><td>3.9</td></tr>
<tr><td>Treated</td><td>10.97 ± 0.18</td><td>48.9</td><td>6.54 ± 0.16</td><td>30.3</td><td>3.25 ± 0.14</td><td>15.0</td><td>0.94 ± 0.07</td><td>4.3</td></tr>
<tr><td>Significance (Cvt)</td><td>NS</td><td></td><td>*</td><td></td><td>**</td><td></td><td>NS</td><td></td></tr>
</table>

<table>
<tr><td></td><td colspan="6">Dissected</td></tr>
<tr><td></td><td colspan="2">Fat</td><td colspan="2">Muscle</td><td colspan="2">Bone</td></tr>
<tr><td></td><td>(g)</td><td>%</td><td>(g)</td><td>%</td><td>(g)</td><td>%</td></tr>
<tr><td>Pre-expt</td><td>636.2</td><td>21.9</td><td>1789.3</td><td>61.6</td><td>478.6</td><td>16.5</td></tr>
<tr><td>Control</td><td>685.1</td><td>23.7</td><td>1830.3</td><td>63.3</td><td>398.5</td><td>13.8</td></tr>
<tr><td>Treated</td><td>536.3</td><td>18.6</td><td>1954.2</td><td>67.6</td><td>377.7</td><td>13.0</td></tr>
<tr><td>Significance (CvT)</td><td colspan="2">0.1</td><td colspan="2">0.1</td><td colspan="2">NS</td></tr>
</table>

*Based on a standard forequarter weight of 2.9 kg.

TABLE 3

<table>
<tr><td colspan="5">The Effect of S-100 Vaccine on Liveweight,<br>Final Liveweight Gain and Carcass Weight</td></tr>
<tr><td colspan="5">Weights of Sheep</td></tr>
<tr><td></td><td>Initial<br>Liveweight<br>(kg)</td><td>Final<br>Gain<br>(kg)</td><td>Liveweight<br>Gain<br>(g/day)</td><td>Carcass<br>Weight<br>(kg)</td></tr>
<tr><td>Pre-expt</td><td>31.3 ± 0.06</td><td colspan="2">Slaughtered at start<br>of study</td><td>12.8 ± 0.45</td></tr>
<tr><td>Control</td><td>31.5 ± 0.58</td><td>50.2 ± 1.07</td><td>132 ± 6.6</td><td>22.1 ± 0.51</td></tr>
<tr><td>Treated</td><td>31.5 ± 0.56</td><td>49.6 ± 0.65</td><td>135 ± 7.0</td><td>21.6 ± 0.22</td></tr>
</table>

The data obtained from the changes in carcass components from the two groups of animals used in Experiments 2-4 was analyzed to disclose the daily rates of change in carcass water, protein, lipid, and ash (Table 5). As is shown in Table 5, animals maintained in a hyperimmune state had approximately twice the daily gain in carcass protein as compared to that of control animals. In addition, the rate of lipid deposition was decreased from 34.2 g/day (d) to 26.0 g/d in the hyperimmune animal.

TABLE 5

<table>
<tr><td colspan="5">Effect of S-100 Vaccine on Daily Mean Rate of Change (g/d)<br>in the Chemical Carcass Components</td></tr>
<tr><td></td><td>Moisture</td><td>Fat</td><td>Protein</td><td>Ash</td></tr>
<tr><td>Control</td><td>22.1</td><td>34.2</td><td>4.13</td><td>1.87</td></tr>
<tr><td>Treated</td><td>24.1</td><td>26.0</td><td>8.69</td><td>2.25</td></tr>
</table>

The data in Table 5 was determined by subtracting the weight of the carcass components of the pre-experimental group from those of the control and treated groups and then dividing by 140 days.

Now having fully described this invention, it will be understood by those with skill in the art that the scope may be performed within a wide and equivalent range of conditions, parameters, and the like, without affecting the spirit or scope of the invention or any embodiment thereof.

What is claimed is:

1. A method for producing lean meat in a bovine or ovine animal comprising immunizing said animal with an antigenic vaccine which induces and maintains the hyperimmune state in said animal.

2. A method for increasing body protein to fat ratio in a bovine or ovine animal comprising immunizing said animal with an antigenic vaccine which induces and maintains the hyperimmune state in said animal.

3. The method of claim 1, wherein said meat is mutton or lamb.

4. The method of claim 1, wherein said meat is beef or veal.

5. The method of claim 2, wherein said animal is a food animal.

6. The method of claim 5 wherein said food animal is growing.

7. The method of claim 5 wherein said food animal is an ovine animal.

8. The method of claim 5 wherein said food animal is a bovine animal.

9. The method of claim 1 or 2 wherein said antigenic vaccine is a microencapsulated polyvalent vaccine.

10. Lean meat harvested from a food animal wherein said lean meat is produced by inducing and maintaining said food animal in a hyperimmune state.

11. The meant of claim 10, wherein said food animal is an ovine animal.

12. The meat of claim 10, wherein said food animal is a bovine animal.

* * * * *